United States Patent [19]

Butcosk

[11] 4,388,198
[45] Jun. 14, 1983

[54] ANTI-RUST ADDITIVES AND COMPOSITIONS THEREOF

[75] Inventor: Richard A. Butcosk, Westmont, N.J.

[73] Assignee: Mobil Oil Corporation, New York, N.Y.

[21] Appl. No.: 54,753

[22] Filed: Jul. 5, 1979

[51] Int. Cl.$^3$ .............................................. C10M 1/10
[52] U.S. Cl. .................................... 252/28; 252/33.6; 252/42
[58] Field of Search .................... 252/28, 33.6, 39, 35, 252/41, 51.5 A

[56] References Cited

U.S. PATENT DOCUMENTS

| 2,490,744 | 12/1949 | Trigg et al. | 252/51.5 A |
| 3,116,247 | 12/1963 | Moore et al. | 252/39 |
| 3,219,666 | 11/1965 | Norman et al. | 252/51.5 A |

Primary Examiner—Charles F. Warren
Assistant Examiner—Y. Harris Smith
Attorney, Agent, or Firm—Charles A. Huggett; Michael G. Gilman; Howard M. Flournoy

[57] ABSTRACT

Reaction products of substituted succinic acid or anhydride with metal hydroxides or amines are highly effective anti-rust agents for lubricating oils or greases prepared therefrom.

14 Claims, No Drawings

ANTI-RUST ADDITIVES AND COMPOSITIONS THEREOF

BACKGROUND OF THE INVENTION

1. Field of the Invention

This invention is directed to lubricant compositions consisting of oils of lubricating viscosity and greases prepared therefrom which provide excellent anti-rust or corrosion characteristics when certain novel additive materials are incorporated therein.

2. Description of the Prior Art

It is known to incorporate into lubricant compositions, for example greases and other lubricants of varying viscosities, various rust or corrosion-inhibiting materials to avoid the deleterious effect of humid or wet environmental conditions upon metal surfaces being lubricated. Among such materials are the alkali metal nitrites, e.g., sodium nitrite. In order to achieve an adequate degree of corrosion-inhibiting effect, the alkali metal nitrite had to be employed in an amount equal to at least 2 percent by weight of the total lubricating composition. However, even such low amounts resulted in the abrasion and deterioration of the metal surfaces coming in contact with such compositions. It was later discovered that this problem could be overcome by using relatively small amounts of alkali metal nitrites in conjunction with a N-carboxymethyl-alkenylsuccinic acid and in alkali metal phosphate (U.S. Pat. No. 3,278,427).

It is also known to use N-carboxymethyl-alkenylsuccinic acid in oils and fuels as an anti-rust agent. However, when it is used in greases in sufficient amounts to prevent rusting, it interferes with the grease thickener and forms a semi-fluid lubricant. In order to overcome this deleterious effect in greases, large quantities of sodium nitrite must be used, as well as a small quantity of N-carboxymethyl-alkenylsuccinic acid.

It has now been discovered that the use of alkali metal nitrites, especially sodium nitrite, can be totally eliminated from anti-rust or corrosion-inhibiting lubricating compositions without sacrificing corrosion-inhibiting effectiveness.

SUMMARY OF THE INVENTION

This application is, therefore, directed to improved anti-rust compositions not having alkali-metal nitrites as corrosion-inhibitors. This application is more particularly directed to improved anti-rust or corrosion-inhibiting compositions comprising a major proportion of an oil of lubricating viscosity or grease prepared therefrom and a minor effective proportion of an anti-rust inhibitor consisting of reaction products of substituted succinic acids or anhydrides with metal hydroxides or amines.

DESCRIPTION OF SPECIFIC EMBODIMENTS

Any suitable succinic acid or anhydride, i.e., any alkenylsuccinic acid or anhydride may be used. Suitable succinic acids or anhydrides have the following general formulae:

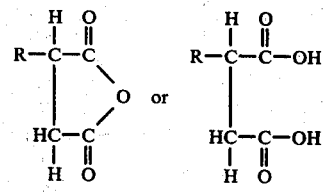

where the alkenyl radical R contains from 2 to about 36 carbon atoms and preferably from 12 to 24.

Suitable amines include any alkyl and aryl or alkaryl amines with the proviso that at least one free hydrogen atom must be present in the amine. Preferred are such amines as morpholine or urea.

Any suitable metal hydroxide or amine may be used in this invention. Suitable metal hydroxides include: aluminum and alkali or alkaline earth metal hydroxides. Preferred are aluminum, lithium, sodium and calcium hydroxides.

The additives in accordance herewith are prepared by reacting a substituted succinic acid, or anhydride or the reaction product of a succinic acid or succinic acid anhydride and an amino acid such as glycine with the metal hydroxide or amine in the following general manner: (1) Metal salts: The metal hydroxide is dissolved in a minimal amount of water and then for example the succinic acid is added, followed with rapid mixing. The water may be removed by heating the mixture to about 250° F.; (2) Amine type salts, etc. The succinic acid, anhydride or reaction product with, for example, glycine is put into solution with benzene or toluene as solvent (although any known suitable solvent may be used), and then the amine material is added with rapid mixing. To form the amide the solution is heated under refluxing for about one hour. The salt is formed by adding additional amine without further heating. The solvent may be removed by distillation. Hereinafter the term substituted succinic acid or anhydride is intended to include reaction products of a succinic acid or anhydride and an amino acid such as glycine.

The following general empirical formulae represent typical embodiments in accordance with this invention and/or embodiments evaluated herein with respect to their corrosion-inhibiting characteristics:

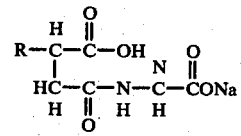

½ sodium salt of N—carboxymethyl-alkenylsuccinic acid.

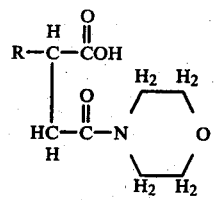

½ acid; ½ amide (morpholine) of alkenylsuccinic acid.

-continued

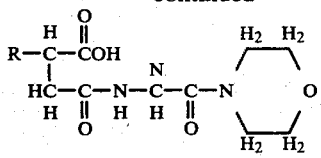

½ acid; ½ amide (morpholine) of
N—carboxymethyl-alkenylsuccinic acid.

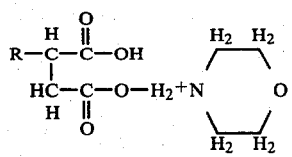

½ acid; ½ salt (morpholine) of
alkenylsuccinic acid.

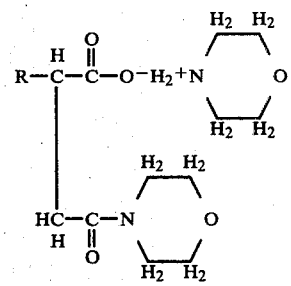

½ salt  
½ amide  } morpholine of alkenylsuccinic acid.

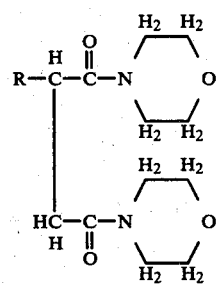

Diamide (morpholine) of alkenylsuccinic acid.

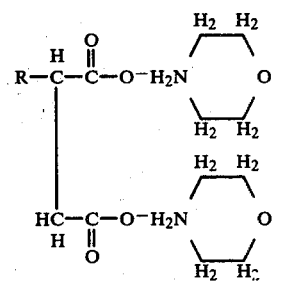

Disalt (morpholine) of alkenylsuccinic acid.

The additives of this invention are effective in amounts from about 0.2 to 5 weight percent and preferably in an amount from about 0.5 to 3 wt. % based on the total weight of the lubricant composition. They may be used alone or in mixtures thereof. They also may be used in compositions containing standard additives for their known use such as E.P. agents, antioxidants and the like.

The novel compounds in accordance with this invention are especially useful in grease formulations, since they do not interfere with the grease thickener. Accordingly, any suitable thickener may be used to prepare grease formulations selected for use with the instant additives. For example, soap and non-soap thickeners may be used. However, especially suitable for use with additives in accordance herein are clays which may be natural, synthetic or chemically modified clays or zeolites.

The following is a non-exhaustive list of suitable naturally occurring clays: clays of the attapulgite, montmorillonite and kaolin families, which families include the sub-bentonites and the kaolins commonly known as Dixie, McNamme-Georgia and Florida clays or others in which the main mineral constituent is halloysite, kaolinite, dickite, illite, nacrite or anauxite and activated carbons, bauxite, attapulgite and fuller's earth. Such clays can be used in the raw state as originally mined or initially subjected to calcination, acid treatment or chemical modification. Especially preferred are clays which are substantially composed of bentonite clays. These clays hereinafter referred to as Baragel clays are more fully described in U.S. Pat. No. 3,449,248 which is incorporated herein in its entirety.

The lubricant compositions useful herein may be derived from mineral or synthetic oils of lubricating viscosity or from mixtures of mineral and synthetic oils or from mineral oil fractions.

The lubricating vehicles employed in grease compositions of the present invention can comprise any of the conventional oils of lubricating viscosity, including mineral or synthetic lubricating oils. Mineral lubricating oils can be of any suitable lubricating viscosity ranging from about 45 SUS at 100° F. to about 3500 SUS at 100° F., and preferably from about 50 to about 250 SUS at 210° F. These oils may have viscosity indexes varying from below 0 to about 130 or higher. Other hyrocarbon oils include synthetic hydrocarbon polymers having improved viscosity indexes, which polymers are prepared by polymerizing an olefin or mixtures of olefins having from 5 to 18 carbon atoms per molecule in the presence of an aliphatic halide and a Ziegler-type catalyst.

The lubricating vehicles employed in novel grease compositions of the present invention can comprise, as previously indicated, synthetic lubricating oils such as polypropylene, polypropylene glycol, di(2-ethylhexyl) sebacate, di-(2-ethylhexyl) adipate and related adipates, dibutyl phthalate, polyethylene glycol, di(2-ethyl hexoate) and polysiloxanes (silicones). An important type of synthetic vehicle that may be employed in conjunction with mineral lubricating oils as a combination of vehicles are esters such as trimethylol propane esters, neopentyl esters and pentaerythritol esters. Other synthetic ester lubricants may include esters of adipic acid and isooctyl and isodecyl alcohols.

It is often advantageous to include in the novel grease compositions of the present invention stabilizing agents such as pentaerythritol. Other improving agents can also be included in the grease compositions of this invention in order to obtain the benefit of their known characteristics.

Having fully described the invention, the following examples are merely illustrative of typical additives in accordance herewith and are intended in no way to limit the scope of this invention.

Examples 1–11 were prepared by reacting glycine and tetrapropenyl succinic anhydride as indicated below. The reaction product thereof was then neutralized with one of the following: morpholene and urea, or lithium, sodium calcium or aluminum hydroxide and thereafter formulated into grease formulations thickened with 10% Baragel clay.

EXAMPLE 1

A mixture of 75 grams (1 mole) of glycine ($NH_2CH_2COOH$) and 268 grams (1 mole) tetrapropenyl succinic anhydride were reacted in accordance with U.S. Pat. No. 3,039,861 (see in particular Example 1 thereof) which is incorporated herein in its entirety.

Aliquots of the reaction product were then neutralized with lithium hydroxide.

A grease comprising Baragel clay 10 wt. % and 3 wt. % lithium salt of the above reaction product was thereafter formulated.

The other examples (2-11) were prepared in similar manner and contained the various salts (additives) in the varying percentages set forth in Table I.

EXAMPLE 12

An ½ acid, ½ amide (morpholine) (see empirical formulae II) of dodecylsuccinic acid was prepared as follows:

The dodecylsuccinic acid was dissolved in minimal amount of benzene and ½ half the stoichiometric equivalent of morpholine was added and stirred rapidly. The mixture was heated, with stirring, to 360° F. to remove the benzene and water of reaction.

EXAMPLE 13

A disalt (morpholine) (see empirical formulae VII) of dodecylsuccinic acid was prepared as follows:

The dodecylsuccinic acid was dissolved in minimal amount of benzene and the stoichiometric equivalent of morpholine was added, with rapid stirring. The benzene was removed under vacuum and a temperature of less than 100° F.

EXAMPLE 14

A diamide (morpholine) (see formulae VI) of dodecylsuccinic acid was prepared as follows:

The dodecylsuccinic acid was dissolved in minimal amount of benzene and the stoichiometric equivalent of morpholine was added, with rapid stirring. The mixture was heated, with stirring, to 360° F. to remove the benzene and the water of reaction.

Examples 1 through 27 were thereafter tested as antirust or anticorrosion additives. Table 1 tabulates the test data for Examples 1 to 11 in a non-soap grease formulation. Table II gives the results using Examples 12, 13, and 14 in a typical lithium soap thickened grease formulation.

Several other additives, Examples 15 to 27, in accordance with this invention were prepared and also tested in non-soap thickened grease formulations for their corrosion inhibiting properties; their test data are set forth in Table III.

Examples 15 through 19 are reaction products of dodecylsuccinic anhydride and morpholine: Example 15—½ acid—½ amide; Example 16—½ salt—½ amide; Example 17— disalt; Example 18— diamide; Example 19—½ acid—½ salt. Examples 20 and 21 are reaction products of a mixture of $C_{18}$ to $C_{24}$ alkenylsuccinic anhydride and morpholine. Example 20—½ acid—½ amide; Example 21—½ salt—½ amide. Examples 22 through 26 are reaction products of dodecylsuccinic acid/glycine and morpholine. Example 22—½ acid—½ amide; Example 23—½ salt—½ amide; Example 24—diamide; Example 25—½ acid—½ salt; Example 26—½ acid—½ salt. Example 27 is a reaction product of dodecylsuccinic anhydride/glycine and morpholine (salt).

From the data of Tables I, II and III it is seen that lubricant compositions, i.e., greases, in accordance with this invention have excellent anticorrosion/anti-rust properties. These novel additives eliminate the use of undesirable sodium nitrate and are compatible with various types of grease thickeners and fluids as well as most of the known special purpose additives.

It is understood that various modification and adaptations may be made without departing from the spirit and scope of this invention.

TABLE I

| | NON-SOAP THICKENED GREASES | | | | | | | | | | |
|---|---|---|---|---|---|---|---|---|---|---|---|
| Example No. | 1 | 2 | 3 | 4 | 5 | 6 | 7 | 8 | 9 | 10 | 11 |
| Baragel Clay (non-soap thickener) % wt. | 10.0 | 10.0 | 10.0 | 7.1 | 9.7 | 10.0 | 10.0 | 10.0 | 9.0 | 8.0 | 5.6 |
| Reaction Product of Glycine and tetrapropenyl succinic anhydride | | | | | | | | | | | |
| Salts of Reaction Product % wt. | | | | | | | | | | | |
| Morpholine | | | 3.0 | | | | | | | | |
| Lithium | 3.0 | 1.5 | | | | | | | | | |
| Sodium | | | | 1.5 | | 0.75 | | | 0.3 | 0.3 | 0.3 |
| Urea | | | | | 1.5 | | | | | | |
| Calcium | | | | | | | 3.0 | | | | |
| Aluminum | | | | | | | | 3.0 | | | |
| Corrosion Test (ASTM D-1743) | | | | | | Pass | | | | | |
| Worked Penetration (ASTM D-217) | — | 275 | 319 | 305 | 265 | — | — | — | 257 | 315 | 265 |

*Pass = no corrosion marks on test bearings
Base Grease: Clay % as indicated, balance a solvent refined mineral oil.

TABLE II

| LITHIUM SOAP THICKENED GREASES | | | |
|---|---|---|---|
| | % Additive Added to Base Grease | | |
| Base Grease* | None | | |
| Base Grease + Example 12 | 0.5 | | |
| Base Grease + Example 13 | | 0.5 | |
| Base Grease + Example 14 | | | 0.5 |
| Corrosion Test (ASTM D-1743) | Fail | Pass | Pass | Pass |

TABLE II-continued

LITHIUM SOAP THICKENED GREASES

| | % Additive Added to Base Grease | | | |
|---|---|---|---|---|
| | 3,3 | 1,1 | 1,1 | 1,1 |

Ratings:
1 = no marks on bearing (no corrosion)
2 = not more than 3 small corrosion marks on bearing
3 = more than 3 corrosion marks on bearing
Base Grease: Baragel clay 10 wt. %, balance a solvent refined mineral oil.

TABLE III

NON-SOAP THICKENED GREASES

| Example No. | Wt. % | Corrosion ASTM D-1743 | Worked Penetration ASTM D-217 |
|---|---|---|---|
| 15 | 2.0 | 1,1 | 313 |
| 16 | 2.0 | 1,1 | 261 |
| 17 | 2.0 | 1,1 | 231 |
| 18 | 2.0 | 1,3 | 243 |
| 19 | 2.0 | 1,1 | 247 |
| 20 | 2.0 | 1,3 | 314 |
| 21 | 1.5 | 1,1 | 284 |
| 22 | 2.0 | 1,1 | 297 |
| 23 | 2.0 | 1,1 | 235 |
| 24 | 2.0 | 1,1 | — |
| 25 | 2.0 | 1,1 | 225 |
| 26 | 0.8 | 1,1 | 290 |
| 27 | 2.0 | 1,1 | — |

Base Grease: Baragel clay - 10.0 wt. %; balance a solvent refined mineral oil.

We claim:

1. A lubricant composition comprising a major proportion of an oil of lubricating viscosity or grease prepared therefrom and a minor effective proportion of a rust or corrosion inhibitor prepared by reacting under suitable conditions a substituted succinic acid or succinic acid anhydride or the reaction product of a succinic acid or succinic acid anhydride, having an alkenyl radical containing from about 2 to 36 carbon atoms, and an amino acid with a metal hydroxide.

2. The composition of claim 1 wherein said composition is a grease.

3. The composition of claim 2 wherein the alkenyl radical of the succinic acid or anhydride contains from 12 to 36 carbon atoms.

4. The composition of claim 3 wherein the alkenyl radical contains 12 carbon atoms.

5. The composition of claim 2 wherein the metal hydroxide is selected from the group consisting of aluminum, calcium, lithium and sodium hydroxides.

6. The composition of claim 5 wherein the metal hydroxide is sodium hydroxide.

7. The composition of claim 2 wherein said composition is thickened by bentonite clay.

8. The composition of claim 7 having at least about 10.0 wt. % of said clay.

9. The composition of claims 2, 3 or 5 wherein said inhibitor is prepared by reacting (1) the reaction product of glycine and tetrapropenyl succinic anhydride and (2) sodium, hydroxide.

10. The composition of claims 1 or 2 wherein the oil of lubricating viscosity is a mineral oil.

11. The composition of claims 1 or 2 wherein the oil of lubricating viscosity is a synthetic oil.

12. The composition of claim 1 having from about 0.5 to 5.0 wt. % of the rust or corrosion inhibitor.

13. An anti-rust additive as prepared in claim 1.

14. The anti-rust additive of claim 13 wherein it is prepared from the reaction product of glycine and tetrapropenyl succinic anhydride and one of the following lithium hydroxide, sodium hydroxide, calcium hydroxide or aluminum hydroxide.

* * * * *